(12) United States Patent
Miao

(10) Patent No.: US 9,644,208 B2
(45) Date of Patent: May 9, 2017

(54) MIRNA FOR REGULATING FABP6 GENE AND METHOD OF USING THE SAME

(71) Applicant: Xiangyang Miao, Beijing (CN)

(72) Inventor: Xiangyang Miao, Beijing (CN)

( * ) Notice: Subject to any disclaimer, the term of this patent is extended or adjusted under 35 U.S.C. 154(b) by 0 days.

(21) Appl. No.: 14/835,681

(22) Filed: Aug. 25, 2015

(65) Prior Publication Data

US 2016/0083727 A1    Mar. 24, 2016

(30) Foreign Application Priority Data

Sep. 19, 2014 (CN) .......................... 2014 1 0480221

(51) Int. Cl.
*A61K 48/00* (2006.01)
*C07H 21/02* (2006.01)
*C07H 21/04* (2006.01)
*C12N 15/113* (2010.01)
*C12Q 1/68* (2006.01)

(52) U.S. Cl.
CPC .......... *C12N 15/113* (2013.01); *C12Q 1/6876* (2013.01); *C12Q 1/6883* (2013.01); *C12N 2310/141* (2013.01); *C12N 2330/10* (2013.01); *C12Q 2600/124* (2013.01); *C12Q 2600/158* (2013.01); *C12Q 2600/178* (2013.01)

(58) Field of Classification Search
CPC ........................... A61K 48/00; C12N 2310/11
See application file for complete search history.

(56) References Cited

U.S. PATENT DOCUMENTS 9,044,492 B2 * 6/2015 Delacote ............ A61K 31/7088

* cited by examiner

*Primary Examiner* — Amy Bowman
(74) *Attorney, Agent, or Firm* — Matthias Scholl, PC; Matthias Scholl

(57) ABSTRACT

A molecular marker miRNA for sheep breeding. The target gene of the miRNA is FABP6, and the miRNA inhibits the expression of the gene FABP6 in the adipose tissue of sheep.

2 Claims, 1 Drawing Sheet

SEQUENCE LISTING

```
<160> NUMBER OF SEQ ID NOS: 12

<210> SEQ ID NO 1
<211> LENGTH: 17
<212> TYPE: RNA
<213> ORGANISM: Artificial Sequence
<220> FEATURE:
<223> OTHER INFORMATION: Fully synthetic

<400> SEQUENCE: 1
uggaccuggg gcucugc                                                  17

<210> SEQ ID NO 2
<211> LENGTH: 50
<212> TYPE: DNA
<213> ORGANISM: Artificial Sequence
<220> FEATURE:
<223> OTHER INFORMATION: Reverse transcription primer of miR-29692

<400> SEQUENCE: 2
gtcgtatcca gtgcagggtc cgaggtattc gcactggata cgacgcagag             50

<210> SEQ ID NO 3
<211> LENGTH: 22
<212> TYPE: DNA
<213> ORGANISM: Artificial Sequence
<220> FEATURE:
<223> OTHER INFORMATION: Forward primer of miR-29692

<400> SEQUENCE: 3
cgggctggac ctggggctct gc                                            22

<210> SEQ ID NO 4
<211> LENGTH: 21
<212> TYPE: DNA
<213> ORGANISM: Artificial Sequence
<220> FEATURE:
<223> OTHER INFORMATION: Reverse primer of miR-29692

<400> SEQUENCE: 4
cgcagggtcc gaggtattcg c                                             21

<210> SEQ ID NO 5
<211> LENGTH: 17
<212> TYPE: DNA
<213> ORGANISM: Artificial Sequence
<220> FEATURE:
<223> OTHER INFORMATION: Forward primer of miR-29692
```

```
<400> SEQUENCE: 5
tggacctggg gctctgc                                                    17

<210> SEQ ID NO 6
<211> LENGTH: 17
<212> TYPE: DNA
<213> ORGANISM: Artificial Sequence
<220> FEATURE:
<223> OTHER INFORMATION: Internal control forward primer

<400> SEQUENCE: 6
ctcgcttcgg cagcaca                                                    17

<210> SEQ ID NO 7
<211> LENGTH: 20
<212> TYPE: DNA
<213> ORGANISM: Artificial Sequence
<220> FEATURE:
<223> OTHER INFORMATION: Internal control reverse primer

<400> SEQUENCE: 7
aacgcttcac gaatttgcgt                                                 20

<210> SEQ ID NO 8
<211> LENGTH: 22
<212> TYPE: RNA
<213> ORGANISM: Artificial Sequence
<220> FEATURE:
<223> OTHER INFORMATION: Fully synthetic

<400> SEQUENCE: 8
ccuugugagc ucuaugcaag gg                                              22

<210> SEQ ID NO 9
<211> LENGTH: 50
<212> TYPE: DNA
<213> ORGANISM: Artificial Sequence
<220> FEATURE:
<223> OTHER INFORMATION: Reverse transcription primer of ssc-miR-28-3p

<400> SEQUENCE: 9
gtcgtatcca gtgcagggtc cgaggtattc gcactggata cgaccccttg               50

<210> SEQ ID NO 10
<211> LENGTH: 24
<212> TYPE: DNA
<213> ORGANISM: Artificial Sequence
<220> FEATURE:
<223> OTHER INFORMATION: Forward primer of ssc-miR-28-3p

<400> SEQUENCE: 10
taccttgtga gctctatgca aggg                                            24

<210> SEQ ID NO 11
<211> LENGTH: 23
<212> TYPE: DNA
<213> ORGANISM: Artificial Sequence
<220> FEATURE:
<223> OTHER INFORMATION: Reverse primer of ssc-miR-28-3p

<400> SEQUENCE: 11
cgcagggtcc gaggtattcg cac                                             23

<210> SEQ ID NO 12
<211> LENGTH: 22
```

```
<212> TYPE: DNA
<213> ORGANISM: Artificial Sequence
<220> FEATURE:
<223> OTHER INFORMATION: Forward primer of ssc-miR-28-3p

<400> SEQUENCE: 12
ccttgtgagc tctatgcaag gg                                              22
```

MIRNA FOR REGULATING FABP6 GENE AND METHOD OF USING THE SAME

CROSS-REFERENCE TO RELATED APPLICATIONS

Pursuant to 35 U.S.C. §119 and the Paris Convention Treaty, this application claims the benefit of Chinese Patent Application No. 201410480221.3 filed Sep. 19, 2014, the contents of which are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND OF THE INVENTION

Field of the Invention

The invention relates to miRNA for regulating FABP6 gene and methods for using the same.

Description of the Related Art

With the improvements in sheep breeding productivity, the quality of sheep meat is adversely affected. The quality of the meat is related to the content and the constituent of the fatty acid and is controlled by minor genes; however, the conventional phenotypic selection fails to improve the fatty acid of the muscle because of correlations among different traits.

Fatty acid binding protein (FABPs) participates in the transport of intercellular fatty acid and most of the FABPs are the primary candidate genes related to the sheep meat. It is a problem to find miRNA molecular markers to regulate the expression of the FABPs gene.

SUMMARY OF THE INVENTION

In view of the above-described problem, it is one objective of the invention to provide a molecular marker miRNA for sheep breeding, and a target gene of the miRNA is FABP6.

In a class of this embodiment, the miRNA is expressed at a low level in an adipose tissue of a fine meat sheep variety; and the miRNA is expressed at a high level in the adipose tissue of a common meat sheep variety and down-regulates the target gene FABP6 expression.

It is another objective of the invention to provide a miRNA marker relating to the muscle quality of sheep. The miRNA is miR-29692 in sheep.

In a class of this embodiment, a sequence of miR-29692 is represented by SEQ ID NO 1, and SEQ ID NO 1: UGGACCUGGGGCUCUGC.

In a class of this embodiment, a target gene of miR-29692 in sheep is FABP6.

In a class of this embodiment, when a stem-loop method is adopted to detect the miR-29692 marker, a sequence of a reverse transcription (RT) primer is represented by SEQ ID NO 2, a forward primer is represented by SEQ ID NO 3, and a reverse primer is represented by SEQ ID NO 4.

In a class of this embodiment, a probe method or a dye method is adopted when using the stem-loop method to detect the miR-29692 marker.

In a class of this embodiment, when a tailing method is used to detect the miR-29692 marker, the forward primer is represented by SEQ ID NO 5.

It is another objective of the invention to provide a real-time fluorescence quantitative (Q)-PCR kit for detecting an expression of miR-29692. The Q-PCR kit comprises a RT reagent, a RT primer, a specific primer, an internal control primer, and a reaction solution for Q-PCR. Preferably, the Q-PCR kit further comprises a specific probe. A sequence of the RT primer is represented by SEQ ID NO 2. The specific primer comprises a forward primer and a reverse primer. The forward primer has a sequence of SEQ ID NO 3, and a reverse primer has a sequence of SEQ ID NO 4.

It is another objective of the invention to provide a Q-PCR kit for detecting the expression of miR-29692. The Q-PCR kit comprises: a RT reagent, a RT primer, a specific forward primer, a universal reverse primer, an internal control primer, and a reaction solution for Q-PCR. A sequence of the specific forward primer is represented by SEQ ID NO 5.

The above reagent kits are applied to quantitative detection of miR-29692 in the adipose tissue in the sheep.

It is still another objective of the invention to provide a miRNA marker relating to the muscle quality of the sheep, and the miRNA is ssc-miR-28-3p in the sheep.

In a class of this embodiment, a sequence of ssc-miR-28-3p is represented by SEQ ID NO 8: CCUUGUGAGCUC-UAUGCAAGGG.

In a class of this embodiment, a target gene of ssc-miR-28-3p is FABP6.

In a class of this embodiment, when the stem-loop method is used to detect the ssc-miR-28-3p marker, a sequence of an RT primer is represented by SEQ ID NO 9, a forward primer is represented by SEQ ID NO 10, and a reverse primer is represented by SEQ ID NO 11.

In a class of this embodiment, when the stem-loop method is adopted to detect the ssc-miR-28-3p marker, the probe method or the dye method is used.

In a class of this embodiment, when the tailing method is used to detect the ssc-miR-28-3p marker, a forward primer is represented by SEQ ID NO 12.

It is still another objective of the invention to provide use of an ssc-miR-28-3p marker or a primer thereof.

To achieve the above purpose, Han sheep and Dorset sheep are herein utilized as the experiment materials. Han sheep is a fine variety features in high content of the intramuscular fat, and Dorset sheep is a variety features in low content of the intramuscular fat. Adipose tissue samples from the backfat are respectively collected from five Dorset sheep and five Han sheep and sent to a sequencing company for high-throughput transcriptome sequencing. The sequencing results are combined with an internationally accepted algorithm EBSeq to analyze the differential gene expression. By analyzing the obviously differentially expressed miR-29692 and ssc-miR-28-3p, the sequences of which are SEQ ID NO 1 and SEQ ID NO 8, respectively, miR-29692 and ssc-miR-28-3p are further used as the study objects. FABP6 is predicted to be the target gene regulated by miR-29692 and ssc-miR-28-3p by searching the RNA hybrid data bank.

The primer sequence is devised according to the above miRNA sequence and the FABP6 sequence.

Expressions of miR-29692, ssc-miR-28-3p, and FABP6 in the abdominal tissues selected from 45 Dorset sheep and 45 Han sheep are detected by RT-PCR method, respectively, and results indicate that the expressions of miR-29692 and ssc-miR-28-3p in the abdominal tissue of the Dorset sheep is obviously higher than in that of the Han sheep, and the former is approximately between 3.23 and 3.58 times of the later.

The experiment results of the inhibition of the expression of gene FABP6 by miRNA indicate that miR-29692 and ssc-miR-28-3p are able to negatively regulate the gene FABP6 alone, and the negative regulation effect is much better when the two cooperatively work, which means that, miR-29692 and ssc-miR-28-3p can be separately or associatively used as markers applied in the generic breeding related to the muscle quality of the sheep.

It is still another objective of the invention to provide a detection kit for detecting a miRNA marker and/or detecting the target gene FABP6. The PCR kit is applicable for all types of fluorescent quantitative gene amplification apparatuses in the current market, and has high sensitivity, fast and accurate quantitation, excellent stability, and good application prospect.

It is still another objective of the invention to provide a method for detecting miR-29692.

In a class of this embodiment, the method for detecting miR-29692 adopts a method based on nucleotide hybridization (such as Northern blot, in situ hybridization, bead-based flow-cytometry, and microarray), splinted ligation, and methods based on PCR (such as RNA tailing, small target quantitative PCR, and stem-loop method), or a combination thereof.

Northern blot is generally conducted as follows: extracting a small RNA having a length of approximately within 200 by from a total RNA using polyacrylamide gel electrophoresis, transferring the small RNA to a blotting membrane to hybridize with a labeled oligonucleotide probe, and analyzing a band after washing and developing the membrane. In order to improve the affinity and the detection sensitivity of the hybridization reaction, a locked nucleic acid (LNA) probe is applied in the analysis research of the miRNA. It is known from the experiment that the introduction of each LNA-modified base into the oligonucleotide probe will result in 1-8° C. of the increase of a melting temperature during hybridization with corresponding DNA and 2-10° C. of the increase of a melting temperature during hybridization with RNA, so that the hybridization specificity and the sensitivity between the LNA probe and the miRNA molecules are improved.

miRNA in situ hybridization is a kind of hybridization that utilizes a colorimetric reagent or a fluorescent reagent labeled DNA probe to hybridize with miRNA in cells or tissues, and detects the expression of miRNA via coloration or fluorescence imaging so as to directly show the spatiotemporal expression of miRNA. The in situ hybridization is capable of displaying the position of the miRNA expression, or even reaching the cell positioning level, thereby being more particularly suitable for paraffin embedded or Formalin fixed specimens.

The bead-based flow-cytometry, i. e., the multi-analyte suspension assay, is a technique that organically combines the flow cytometry with the chip technology, to transform the biochip reaction system from the liquid-solid reaction into a total liquid-phase reaction system which is the most similar to the inner environment of the biological system. Such method utilizes polystyrene beads as reaction carriers, and different beads are labeled with different fluorescent codings that can be identified by corresponding detection systems. The bead can be connected to DNA probes or proteins. The bead is connected to a miRNA capturing probe having a length of 10-12 nt when it is supposed to detect the miRNA. The probe is complementary to the 3'-end of the miRNA and is added with a reporter probe having a length of 8-10 nt to react with the 5'-end of the miRNA. After the reaction, the classified fluorescence of the probes and the labeled fluorescence of the reporter probe on the beads are detected by two laser beams, respectively, in the detection system, thereby realizing the qualitative and quantitative detections of the target miRNA.

The microarray technology is also called the biochip, DNA chip, or gene chip technology. Generally, DNA probes with known sequences in high density arrangement are fixed on a solid supporting material, such as a glass piece, multiple miRNA target molecules are hybridized with the microarray based on the hybridization principles. By detecting the hybridization signal intensity and processing the data, expression profiles of the specific miRNA in different specimens are acquired, so that differences in the miRNA expressions are comprehensively compared between different organs or tissues and between normal tissues and pathological tissues. The microarray technology is advantageous in high throughput, i. e., the whole genome of human being can be analyzed for once, and expressions of more than thirty thousand of genes can be quantitatively acquired in ten minutes.

In the splinted-ligation technique, a segment of deoxynucleotide (a bridge fragment) is pre-designed, and this bridge fragment comprises a 14 nt extension segment at the 5'-end as well as a 3'-end complementary to the target miRNA. In addition, a second depxynucleotide segment (junction fragment) complementary to the 14 nt extension segment is devised, and a 5'-end thereof is labeled with $32^P$. During the annealing, the miRNA and the junction fragment are simultaneously complementary with the bridge fragment, so that a heteroduplex is produced, and a gap exists in the middle of one strand, that is, the juncture between miRNA and the junction fragment. The gap is repaired by a T4DNA ligase, which is equivalent to label miRNA with $32^P$. Free junction fragment labeled by $32^P$ is removed by phosphatase, and polyacrylamide gel electrophoresis is then carried out. The intensity of the radioactive signal is detected, so as to acquire the information corresponding to the amount of miRNA. This method is much simpler, faster, and more sensitive than the Northern blot and can be used to carry out detection of a large amount of specimen.

Tailing method. miRNA has a length of only 22 nt, which is only corresponding to the length of a primer, so that miRNA cannot be detected by conventional RT-PCR. miRNA can be detected using RNA tailing and primer extension RT-PCR. The total RNA is firstly extracted, followed with the small RNA. A segment of the poly A is added at the 3'-end of the small RNA as a tail by the poly A polymerase, and miRNA is reversely transcribed into cDNA by a long primer with a 3'-end containing a segment of poly T. The length of the acquired cDNA is suitable for Q-PCR.

The small target quantitative PCR comprises three steps: reverse transcription, connecting to a DNA template, and PCR amplification of a connecting product. Each reaction is separated from another reaction by deactivation. During the reverse transcription, miRNA is reversely transcribed into cDNA by the specific primer. Because miRNAs are different in at least one base, and the differences are mostly in the 3'-end of miRNA, thus, the terminal of the primer should be within the hypervariable (HVR) region or the vicinity thereof at the 3'-end of miRNA and the length of the primer should be as short as possible. In the second step of the reaction, the cDNA is complementary pairing with the two oligonucleotides, and after the complementary pairing, the gap between the two oligonucleotides reaches the length of 7 nucleotides. Each oligonucleotide is partially pairing to the cDNA, and the remaining part exceeding the length of the cDNA is exposed, which is called M13+. The gap is then filled by T4 DNA ligase, the connecting reaction is very sensitive to the mis-match of the bases at the two ends of the gap, particularly the 3'-end, therefore, the 3'-end of the gap should be arranged at the HVR region of the miRNA to the utmost. In the third reaction, PCR amplification is performed using the connecting product as the template, the forward primer and the reverse primer of the M13+ as the universal PCR primers, and the specific TaqMan probes. Because both the reverse transcription and the connecting reaction use the center of the miRNA and the 3'-end thereof that is the main region to distinguish the miRNA member as the specific target, and the T4 DNA ligase is capable of distinguishing the mismatch of the bases, thus, such the method has relatively high specificity, low cross reaction rate, and can be used as the method for quantitatively detecting the sensitivity of the short nucleotide.

The stem-loop method features in using a single stem-loop primer to avoid tailing the target miRNA. The reaction process is divided into two steps: first, the stem-loop primer is combined with the 3'-end of the target miRNA molecule, 6 complementary base pairings are formed at the 3'-end of the primer and the 3'-end of the miRNA, and the miRNA is then reversely transcribed into a first strand of cDNA by the reverse transcriptase; and second, the PCR reaction is performed. The strand length is increased when the stem-loop structure of the first strand of the cDNA is expanded, and the conventional Q-PCR is performed using the expanded stem-loop structure as the template. The stem part of the stem-loop primer is in a double-strand structure preventing the primer to hybridize with the pre-miRNA or other long stranded RNA. The base stacking at the stem part enhances the affinity of a miRNA-DNA heteroduplex, thereby improving the efficiency of the reverse transcription. The length of the miRNA is increased after the expansion of the stem-loop structure, and then the miRNA participates in the PCR working as a suitable template.

In a class of this embodiment, the expressions of miR-29692 and/or ssc-miR-28-3p are detected by fluorescent quantitation.

In a class of this embodiment, the expression of miR-29692 is detected by the tailing method of the RT-PCR.

In a class of this embodiment, the tailing method for detecting the expression of miR-29692 comprises the following steps: 1) extracting the small RNAs from the adipose tissue of the sheep; 2) tailing and reversely transcribing miR-29692 using a poly(A) polymerase and a reverse transcriptase; and 3) amplifying miR-29692 using SEQ ID NO 5 and a commercially available Q-PCR kit applicable for the tailing method.

In a class of this embodiment, the tailing method for detecting the expression of miR-29692 comprises the following steps: 1) extracting the small RNAs from the adipose tissue of the sheep; 2) tailing and reversely transcribing miR-29692 using a miScript II RT kit provided by Qiagen; and 3) amplifying miR-29692 using the SEQ ID NO 5 and a miScript SYBR Green PCR Kit provided by Qiagen.

In a class of this embodiment, the stem-loop method for detecting the expression of miR-29692 comprises the following steps: 1) extracting the total RNAs from the adipose tissue of the sheep; 2) reversely transcribing miR-29692 using SEQ ID NO 2 as the RT primer under the action of a reverse transcriptase; and 3) amplifying miR-29692 using SEQ ID 3 and SEQ ID NO 4 as the primers and a commercially available Q-PCR kit suitable for the stem-loop method.

In a class of this embodiment, the expression of ssc-miR-28-3p is detected by the tailing method of the RT-PCR.

In a class of this embodiment, the tailing method for detecting the expression of ssc-miR-28-3p comprises: 1) extracting the small RNAs from the adipose tissue of the sheep; 2) tailing and reversely transcribing ssc-miR-28-3p using a poly(A) polymerase and a reverse transcriptase; and 3) amplifying ssc-miR-28-3p using SEQ ID NO 12 and a commercially available Q-PCR kit applicable for the tailing method.

In a class of this embodiment, the tailing method for detecting the expression of ssc-miR-28-3p comprises the following steps: 1) extracting the small RNAs from the adipose tissue of the sheep; 2) tailing and reversely transcribing ssc-miR-28-3p using a miScript II RT kit provided by Qiagen; and 3) amplifying ssc-miR-28-3p using the SEQ ID NO 12 and a miScript SYBR Green PCR Kit provided by Qiagen.

In a class of this embodiment, the stem-loop method for detecting the expression of ssc-miR-28-3p comprises the following steps: 1) extracting the total RNAs from the adipose tissue of the sheep; 2) reversely transcribing ssc-miR-28-3p using SEQ ID NO 9 as the RT primer under the action of a reverse transcriptase; and 3) amplifying ssc-miR-28-3p using SEQ ID 10 and SEQ ID NO 11 as the primers and a commercially available Q-PCR kit suitable for the stem-loop method.

It is still another objective of the invention to provide a method for improving a meat quality of the sheep comprising applying miR-29692 and/or ssc-miR-28-3p as molecular markers.

In a class of this embodiment, in the method for improving a meat quality of the sheep, miR-29692 and/or ssc-miR-28-3p are low expressed and FABP6 is highly expressed in the adipose tissue of the target meat sheep.

Definitions of miRNA and Precursor Thereof

The invention provides a kind of miRNA relating to the meat quality of sheep. As used in the invention, the "miRNA" is a group of small non-coding single strand RNA molecule containing approximately between 19 and 25 nucleotides widely existing in plants, nematodes, drosophilas, and mammals. The miRNA mainly combines with a 3'-UTR region of the encoding protein mRNA via the basically complementary mode to cause the degradation, activity decrease, or translation inhibition of the target mRNA, so as to regulate a group of RNA molecules via the gene expression after the transcription. The mature miRNA generally contains between 19 and 25 nucleotides (nt) (approximately between 19 and 22 for special ones), while other nucleotide numbers are not excluded.

miRNA can be obtained from processing of a precursor miRNA (pre-miRNA). The pre-miRNA can be folded into a stable stem-loop (hairpin) structure. The stem-loop structure generally has a length of between 50 and 100 bp. The pre-miRNA can be folded into a stable stem-loop structure. Two sides of the stem part of the stem-loop structure contain two basically complementary sequences. The pre-miRNA is natural or artificial.

The pre-miRNA can be cut into miRNA. The miRNA is basically complementary to at least one part of the sequence of the gene encoding miRNA. Herein, the "basically complementary" means that the two nucleotide sequences are sufficiently complementary and interact with each other in a predictable mode, for example, forming a secondary structure such as the stem-loop structure. Generally, at least 70% of the nucleotides in the two basically complementary nucleotide sequences are complementary to each other; preferably, at least 80% of the nucleotides of the two sequences are complementary; and more preferably, the proportion reaches 90%; and still more preferably, the proportion reaches at least 95%, such as 98%, 99%, and 100%. Generally speaking, at most 40 unmatched nucleotides are permitted to exist in the two sufficiently complementary molecules; preferably, at most 30 unmatched nucleotides exist; more preferably, at most 20 unmatched nucleotides exist; and more preferably, at most 10 unmatched nucleotides exist, for example, 1, 2, 3, 4, 5, 8, and 11 unmatched nucleotides exist.

The stem-loop structure is also called the hairpin structure, which means a nucleotide molecule capable of forming a secondary structure containing a double-strand region (the stem part). The double-strand region is formed by two regions of the same nucleotide molecule, and the two regions are arranged at two sides of the double-strand region. Furthermore, the hairpin structure further comprises a loop structure, which comprises a noncomplementary nucleotide sequence, i. e., the single strand region. Even the two regions of the nucleotide molecule are not totally complementary to each other, and the double-strand region of the nucleotide molecule is able to remain the double-strand state. Such as, insertion, deletion, substitution, etc., may lead to dismatch in a small region, self-formation of a stem-loop structure or other secondary structure in the small region. However, the two regions are basically complementary to each other, and interact with each other in a predictable mode, and form the double-strand region in the stem-loop structure. The stem-loop structure is well-known by the persons skilled in the art, and generally the persons skilled in the art are able to determine whether the nucleotide is able to form the stem loop structure after the nucleotide sequence in a primary structure is acquired.

Small RNA Sequencing

The small RNA is a group of important regulatory molecules in vivo, and primarily comprises: miRNA, piRNA, and siRNA. The main function thereof is inducing gene silencing, involving in post-transcriptional gene regulation, and therefore regulating the important biological processes such as the cell growth, differentiation, ontogeny, and reproduction. The small RNA sequencing technology adopts the gel extraction technology, 18-30 nt RNA segment is collected from the sample, and high throughput sequencing technology is adopted to acquire information of millions of small RNA sequences of the single-base resolution for one time. The known small RNA is identified, relying on a strong bioinformatics analysis platform, and the new small RNA and the target gene thereof are predicted.

miRNA herein further comprises a miRNA variant and a derivative thereof. In addition, the general miRNA derivative comprises the miRNA variant. Persons skilled in the art are able to modify the miR-29692 using universal method. The modification comprises: methylation modification, hydrocarbon modification, glycosylation modification (e.g. 2-methoxy-glycosyl modification, hydrocarbon-glycosyl modification, sugar-ring modification, etc.), nucleic acid modification, peptide modification, lipid modification, halogen modification, nucleic acid modification like "TT" modification, and others.

Construct of Polynucleotide

According to the miRNA sequence provided in the invention, a polynucleotide construct of the miRNA is devised and the polynucleotide construct is formed after introduction and is able to affect the expression of the corresponding mRNA, that is, the polynucleotide construct is able to regulate the amount of the corresponding miRNA in vivo. The polynucleotide construct can be transcribed into the pre-miRNA by animal cells, and the pre-miRNA can be further cut and express the miRNA by the animal cells.

Generally, the polynucleotide construct is carried by the expression vector. Thus, the invention also provides a vector which comprises the miRNA or the polynucleotide construct. The expression vector generally comprises a promoter, and a replication origin, and/or a marker gene. The expression vector necessitated herein in the invention can be constructed using methods well-known by the persons skilled in the art, such as the in vitro recombinant DNA technology, the DNA synthesis techniques, and in vivo recombination technology, etc. The expression vector preferably comprises one or multiple selectable marker genes, so as to provide selectively convertible phenotypic traits of the host cells, such as resistances of kalamycin, gentamicin, hygromycin, and ampicillin.

Advantages according to embodiments of the invention are summarized as follows:

(a) miR-29692 and/or ssc-miR-28-3p provided in the invention are well correlated with the muscle quality of the sheep and are applicable to genetic marker-assisted breeding related to the muscle quality of the sheep.

(b) The Q-PCR kit for detecting the expression of miR-29692 and/or ssc-miR-28-3p provided by the invention comprises the whole kits for extracting from RNA in the fluorescent quantitative experiment, which is not only convenient for use, but also ensuring the consistency of the results.

BRIEF DESCRIPTION OF THE DRAWINGS

The invention is described herein below with reference to the accompanying drawings, in which.

DETAILED DESCRIPTION OF THE EMBODIMENTS

Figure 1:
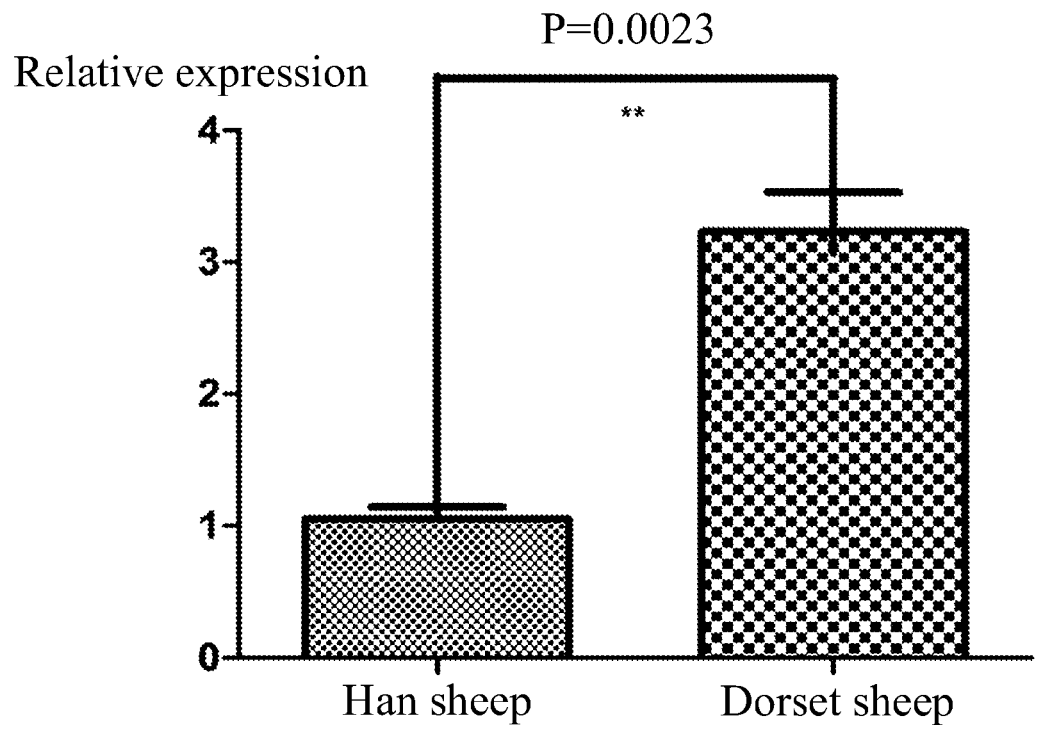
FIG. 1 shows relative expression of miR-29692 in adipose tissue of sheep detected by Real-time PCR.

For further illustrating the invention, experiments detailing miRNA for regulating FABP6 gene and a method for using the same are described below. It should be noted that the following examples are intended to describe and not to limit the invention.

Example 1

High-Throughput Transcriptome Sequencing for Differential Expression miRNA Profiling in Abdominal Fat Tissues of Different Sheep Varieties Abdominal fat tissues were extracted from five Dorset sheep and five Han sheep, respectively. The tissue specimens were divided into small masses respectively and frozen in liquid nitrogen for 30 seconds, and then preserved in a refrigerator at a temperature of −70° C. Small RNA sequencing was performed by a sequencing company.

The quality of the sequencing data were integrally assessed using the Fast-QC software (http://www.bioinformatics.babraham.ac.uk/projects/fastqc/), and the integral assessment included the distribution of the mass value of the base, the position distribution of the mass value, the GC content, the PCR duplication content, the k-mer frequency, etc.

Analysis results of the mature small RNA having the sum of the counts smaller than 10 were deleted, and differential screen was performed combining with the internationally accepted algorithm EBSeq, in which log FC>1 or Log FC<−1, and FDR<0.05. miR-29692 and ssc-miR-28-3p that were significantly differentially expressed were finally screened from the analysis, and the sequences thereof were SEQ ID NO 1 and SEQ ID NO 8, respectively. It was predicted by searching the RNA hybrid data bank that the miR-29692 and ssc-miR-28-3p cooperatively regulate the target gene FABP6.

Example 2

Expressions of miR-29692, Ssc-miR-28-3p, and FABP6 in the Adipose Tissue of the Sheep Detected by Real-Time PCR Reagents:
RT reagent kit:
SG One-Step miRNA RT Kit, #33-30120, SinoGene
PCR Mix: 2×SG PCR MasterMix, #33-10201, SinoGene
qPCR reagent: 2×SG Green qPCR Mix (with ROX), #22-10102, SinoGene Treatment of experiment instruments for removing Rnase:
1) The laboratory glassware was washed and soaked with DEPC solution, and pressurized at 120° C. for 20 min, and then baked at 180° C. for more than 2 hrs; and
2) The plastic containers (such as EP tube/a pipet tip) were washed in 0.1% DEPC and soaked for overnight, naturally dried, pressurized at 120° C. for 20 min, and then baked.

The adipose tissue samples were extracted from 45 Dorset sheep and 45 Han sheep, numbered, and then the samples were randomly selected to extract the RNA. Each adipose tissue sample was treated as follows:

miRNA Extraction:
1) The adipose tissue sample was taken out from the liquid nitrogen, weighed, and placed in centrifuge tubes. Trizol solution was added to the centrifuge tube according to 50-100 mg of the tissue per mL of the amount of Trizol. The tissue volume was not allowed to exceed 10 v. %, and a mixture thereof was homogenized for between 1 and 2 min.
2) The tissue added with the Trizol was incubated at 15-30° C. for 5 min to make the tissue fully decomposed.
3) A miRNA homogenate additive having a volume of 1/10 of that of a mixture in the tube was added and then swirled for several times so as to uniformly mix a resulting mixture, and the centrifuge tube was placed on the ice for 10 min.
4) Trichloromethane having the same volume as that of resulting composed substances in the centrifuge tube was added, and swirled for between 30 and 60 s for uniform mixing.
5) The centrifuge tube was centrifuged for 5 min at the room temperature at a maximum rotational speed (10000 g), so as to separate a water phase from an organic phase and to separate out a middle phase. If the middle phase was not separated out, another centrifuging process was performed.
6) The water phase in the upper layer was sucked and transferred to a new collection tube, and a volume of the water phase water recorded.
7) Anhydrous alcohol having a volume of 1/3 of that of the water phase was added, and a mixed solution was swirled or inverted for several times for uniform mixing.
8) The decomposed solution/alcohol mixed solution was added to a filter core for filtration. The filter core was placed in a new collection tube, and each sample was provided with one filter core.
9) A pipet was used to transfer the mixed solution in the above step to the filter core having a volume capacity of 700 μL for once. Additional mixed solution exceeding 700 μL was continuously filtered by the same filter core.
10) The solution was allowed to pass through the filter core by centrifuging at a rotational speed of 1000 g for 15 s.
11) A filtrate was collected. If the volume of the decomposed solution/alcohol mixed solution was larger than 700 μL, a new collection tube was adopted in continuous filtration till all the decomposed solution/alcohol mixed solution was filtrated, the filtrate was collected, and the volume was recorded.
12) To the filtrate collected from the above step, anhydrous alcohol having a volume of 2/3 of that of the filtration was added at the room temperature.
13) The filtrate/alcohol mixed solution was added to a second filter core for filtration, a filtrate was discarded. Each sample was provided with a filter core, and the filter core is placed in a new collection tube.
14) A pipet was used to transfer the mixed solution in the above step to the filter core having a volume capacity of 700 μL for once. Additional mixed solution exceeding 700 μL was continuously filtered by the same filter core.
15) The solution was allowed to pass through the filter core by centrifuging at a rotational speed of 10000 g for 15 s.
16) A filtrate obtained from the filtration was discarded, and the filter core was kept for conducting elution in a subsequent step.
17) 700 μL of miRNA washing liquid 1 (alcohol was added to a working solution) was added to the filter core, and centrifuged for between 5 and 10 s. A liquid produced in the elution was discarded, and the collection tube was continuously used.
18) 500 μL of miRNA washing liquid 2/3 (alcohol was added to a working solution) was added to the filter core, and centrifuged for between 5 and 10 s. A liquid produced in the elution was then discarded.
19) The above step was repeated.
20) The filter core was placed in a new collection tube (provided in the reagent kit). 100 μL of a preheated washing liquid at 95° C. or water not containing nuclease was added to the filter core, and was thereafter centrifuged at a maximum rotational speed for between 20 and 30 s so as to collect a RNA dissolved solution.

Preparation of RT-PCR System for miRNA

| | |
|---|---|
| 2× SG Green qPCR Mix | 10 μL |
| Forward Primer (10 μM) | 0.4 μL |
| Reverse Primer (10 μM) | 0.4 μL |
| ROX | 0.4 μL |
| cDNA | 1 μL |
| Water, nuclease-free | 7.8 μL |
| Total volume | 20 μL |

Three parallel reaction tubes were provided in order to detect the expression of miRNA, and U6 was adopted as an internal control primer.

Parameters of the PCR program were as follows:
95° C. for 10 min, 45 cycles (95° C. for 15 s, 60° C. for 15 s, 72° C. for 45 s), 95° C. for 15 s, 60° C. 30 s, and 95° C. for 15 s.

Figure 2:
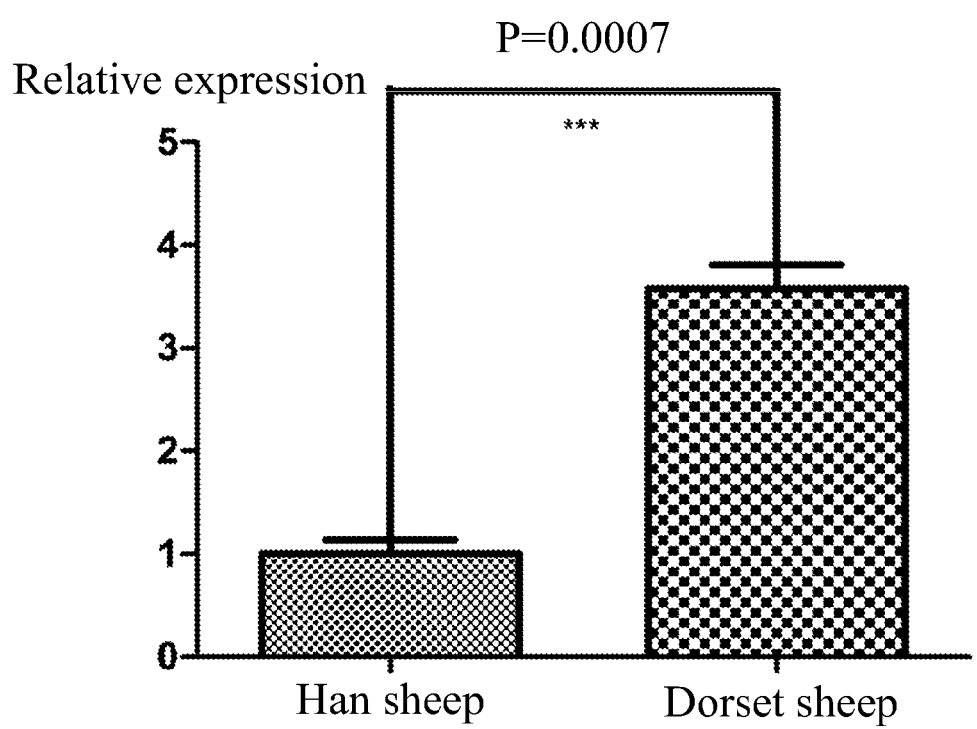
FIG. 2 shows relative expression of ssc-miR-28-3p in adipose tissue of sheep detected by Real-time PCR.

Statistics Analysis
Software OriginPro8.1 was utilized for analysis. The statistical method adopted t-test to perform means comparison, $P<0.05$ (the difference is significant) and $P<0.01$ (the difference is very significant) were defined to have statistical significance. Expressions of miR-29692, ssc-miR-28-3p, and FABP6 in the adipose tissues of sheep of different varieties were analyzed, and results thereof were illustrated in FIG. 1-2, and Table 1:

TABLE 1

Statistical results of relative expression of miRNA

| Samples | chr13_29692 | ssc-miR-28-3p |
|---|---|---|
| Han sheep | 1.057 ± 0.0895 | 1.000 ± 0.1353 |
| Dorset sheep | 3.23 ± 0.3002 | 3.577 ± 0.2341 |

Expressions of miR-29692 and ssc-miR-28-3p in the adipose tissues were obviously higher in Dorset sheep than in Han sheep, specifically, the expression of miR-29692 in the adipose tissue of Dorset sheep was 3.23 times of that in the adipose tissue of Han sheep, and the expression of ssc-miR-28-3p in the adipose tissue of Dorset sheep was 3.58 times of that in the adipose tissue of Han sheep.

Example 3

Inhibition of Expression of FABP6 Gene by Two miRNA

1. Construct of plasmid and synthesis of miRNA

A plasmid vector was pcDNA3.1, a green fluorescent protein (GFP) was connected to the vector by EcoRI and NotI, and a 3'UTR sequence of the FABP6 gen was connected to the vector by restriction sites of XhoI and XbaI to form a vector pcDNA3.1-GFP-3'UTR. The 3'UTR sequence ranges from a first base behind a stop codon to a last base of mRNA.pcDNA3.1-GFP-3'UTR was sent to a specialized company for synthesizing miR-29692 and ssc-miR-28-3p, and a synthetic miRNA mimics was then diluted.

2. Experiment Using GFP as Reporter Gene

Mouse fibroblasts was inoculated to a 24-hole plate with a density of $2.5 \times 10^5$ cells/mL in each hole before transfection, and incubated in a DMEM culture solution containing 10% fetal bovine serum for overnight at 37° C., 5% $CO_2$, and saturated humidity until 70%-80% cells were merged. The cell culture solution was removed and washed using a PBS buffer solution preheated to 37° C. for two times, and thereafter cells were transfected. Cells in each hole were added and uniformly mixed with 200 ng-500 ng of the vector pcDNA3.1-GFP-3'UTR and 100 nM synthetic miRNA, and were diluted with 100 μL of DMEM excluded from antibodies and serum. In the meanwhile, Liposome 2000 (Lipofectamin™ 2000) transfection reagent was diluted by 100 μL of DMEM excluded from antibodies and serum, and the diluted transfection reagent was added to each hole according to a ratio of 1:2.5, so that DMEM containing the vector, the synthetic miRNA, and the liposome were uniformly mixed, and then incubated for 20 min at the room temperature to form a complex. The complexes were added to the cells, slightly mixed, and incubated for 5 hrs at 37° C. and 5% $CO_2$, and a DMEM culture solution was then replaced with a 2% of the fetal bovine serum. 24 hrs and 48 hrs after the transfection, the cells were observed under a fluorescent microscope, and a judge was made according to the GFP positive cell numbers and the intensity of the fluorescence.

3. Results

Fluorescence-positive cells appeared in the transfected cells 24 hrs after the transfection. It is known from results of the fluorescent microscope observation 48 hrs after the transfection.

Compared with the positive control group which is only transfected by the vector pcDNA3.1-GFP-3'UTR, the number of the GFP-positive cells were reduced in the transfected cell culture medium containing the vector pcDNA3.1-GFP-3'UTR and the synthesized miRNA (miR-29692 or ssc-miR-28-3p), and the number of the GFP-positive cells were significantly reduced in the transfection culture medium containing the vector pcDNA3.1-GFP-3'UTR and the synthesized miRNA (miR-29692 and ssc-miR-28-3p).

Example 4

Reagent Kits for Detecting miR-29692 (Tailing Method)

Reagent kit for extracting a small RNA: mirVana™ miRNA Isolation Kit

Reverse Transcription and RT-PCR:

| | | |
|---|---|---|
| 1 | Reaction solution for reverse transcription | miScript Reverse Transcriptase Mix; miScript HiSpec Buffer; Nucleics Mix; Nuclease-free H2O |
| 2 | Forward primer SEQID NO 5 | TGGACCTGGGGCTCTGC |
| 3 | Forward internal control primer SEQ ID NO 6 | CTCGCTTCGGCAGCACA |
| 4 | Reverse internal control primer SEQ ID NO 7 | AACGCTTCACGAATTTGCGT |
| 5 | Reaction solution for qRT-PCR | 2x LightCycler ® 480 SYBR Green I Master; Universal primer; Nuclease-free H2O |

Example 5

Reagent Kits for Detecting miR-29692 (Stem-Loop Method)

Reagent kit for extracting a total RNA: TRIzol, Invitrogen company in the US.

Reverse Transcription and RT-PCR:

| 1 | RT primer SEQID NO 2 | GTCGTATCCA GTGCAGGGTC CGAGGTATTC GCACTGGATA CGACGCAGAG |
| 2 | Reaction solution for reverse transcription | 5× PrimeScript Buffer2; PrimeScript RT Enzyme Mix; RNase FreedH2O |
| 3 | Forward primer SEQID NO 3 | CGGGCTGGACCTGGGGCTCTGC |
| 4 | Reverse primer SEQID NO 4 | CGCAGGGTCCGAGGTATTCGC |
| 5 | Reaction solution for qRT-PCR | 2× All-in-one qPCR Mix; Nuclease-free H2O |

Example 6

Reagent Kits for Detecting Ssc-miR-28-3p (Tailing Method)

Reagent kit for extracting a small RNA: mirVana™ miRNA Isolation Kit

Reverse Transcription and RT-PCR:

| 1 | Reaction solution for reverse transcription | miScript Reverse Transcriptase Mix; miScript HiSpec Buffer; Nucleics Mix; Nuclease-free H2O |
| 2 | Forward primer SEQID NO 12 | CCTTGTGAGCTCTATGCAAGGG |
| 3 | Forward internal control primer SEQID NO 6 | CTCGCTTCGGCAGCACA |
| 4 | Reverse internal control primer SEQID NO 7 | AACGCTTCACGAATTTGCGT |
| 5 | qRT-PCR reaction solution | 2× LightCycler ® 480 SYBR Green I Master; Universal primer; Nuclease-free H2O |

Example 7

Reagent Kits for Detecting Ssc-miR-28-3p (Stem-Loop Method)

Reagent kit for extracting a total RNA: Trizol, Invitrogen Invitrogen company in the US Reverse Transcription and RT-PCR:

| 1 | RT primer SEQID NO 9 | GTCGTATCCA GTGCAGGGTC CGAGGTATTC GCACTGGATA CGACCCCTTG |
| 2 | Reaction solution for reverse transcription | 5× PrimeScript Buffer2; PrimeScript RT Enzyme Mix; RNase FreedH2O |
| 3 | Forward primer SEQID NO 10 | TACCTTGTGAGCTCTATGCAAGGG |
| 4 | Reverse primer SEQID NO 11 | CGCAGGGTCCGAGGTATTCGCAC |

-continued

| 7 | qRT-PCR reaction solution | 2× All-in-one qPCR Mix; Nuclease-free H$_2$O |

The invention analyzed the high throughput sequencing results by adopting the biological information to screen the molecular marker miR-29692 applicable for genetic marker-assisted breeding in the meat sheep, and also provided the Q-PCR kit for detecting the expression of miR-29692. The reagent kit comprises the whole suit of reagents utilized in experiments from the extraction of RNA to the reverse transcription and the fluorescence quantitative experiment, thereby bring convenience in use, ensuring the consistency of the results, and possessing good application prospect.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for promoting or enhancing expression of gene FABP6 within a meat sheep tissue, the method comprising delivering miRNA inhibitors to the meat sheep tissue to inhibit functions of a molecular marker of miR-29692 or ssc-miR-28-3p, wherein a sequence of miR-29692 is represented by SEQ ID NO: 1, and a sequence of ssc-miR-28-3p is represented by SEQ ID NO: 8.

2. A method for promoting or enhancing expression of gene FABP6 within a meat sheep tissue, the method comprising delivering miRNA inhibitors to the meat sheep tissue to inhibit functions of a combination of miR-29692 and ssc-miR-28-3p, wherein a sequence of miR-29692 is represented by SEQ ID NO: 1, and a sequence of ssc-miR-28-3 p is represented by SEQ ID NO: 8.

* * * * *